United States Patent
Iannarone

(10) Patent No.: US 8,048,079 B2
(45) Date of Patent: Nov. 1, 2011

(54) RETROGRADE CUTTING INSTRUMENT

(75) Inventor: Ronald C. Iannarone, Aiken, SC (US)

(73) Assignee: Arthrex, Inc., Naples, FL (US)

( * ) Notice: Subject to any disclaimer, the term of this patent is extended or adjusted under 35 U.S.C. 154(b) by 743 days.

(21) Appl. No.: 12/132,472

(22) Filed: Jun. 3, 2008

(65) Prior Publication Data
US 2008/0306483 A1    Dec. 11, 2008

Related U.S. Application Data

(60) Provisional application No. 60/942,614, filed on Jun. 7, 2007.

(51) Int. Cl.
*A61B 17/16* (2006.01)
(52) U.S. Cl. ...................... 606/80; 623/13.11
(58) Field of Classification Search .............. 623/13.11, 623/13.12, 13.14; 606/79, 80, 83, 86 R, 606/88, 167, 170, 84–85
See application file for complete search history.

(56) References Cited

U.S. PATENT DOCUMENTS

| | | |
|---|---|---|
| 5,549,613 A | 8/1996 | Goble et al. |
| 6,015,411 A | 1/2000 | Ohkoshi et al. |
| 6,162,227 A * | 12/2000 | Eckhardt et al. ............. 606/84 |
| 6,332,886 B1 * | 12/2001 | Green et al. .................. 606/80 |
| 2004/0176771 A1 | 9/2004 | Schmieding |
| 2005/0154398 A1 | 7/2005 | Miniaci et al. |
| 2006/0085006 A1 | 4/2006 | Ek et al. |
| 2006/0195112 A1 | 8/2006 | Ek |
| 2007/0123921 A1 | 5/2007 | Ek |
| 2007/0250067 A1 * | 10/2007 | Schmieding et al. .......... 606/96 |
| 2008/0183174 A1 | 7/2008 | Sikora et al. |
| 2008/0306483 A1 | 12/2008 | Iannarone |
| 2009/0171359 A1 | 7/2009 | Sterrett |

FOREIGN PATENT DOCUMENTS

| | | |
|---|---|---|
| EP | 1 987 786 A3 | 11/2008 |
| WO | WO 2006/074321 | 7/2006 |
| WO | WO 2006/124937 | 11/2006 |
| WO | WO 2008/076330 | 6/2008 |

* cited by examiner

*Primary Examiner* — Thomas C. Barrett
*Assistant Examiner* — Christian Sevilla
(74) *Attorney, Agent, or Firm* — Dickstein Shapiro LLP

(57) ABSTRACT

An instrument for retrograde cutting of sockets or tunnels in bone for arthroscopic tenodesis. A retrograde cutter is used to form a recipient site socket from the inside out, i.e., using a retrograde technique, with minimal incisions of distal cortices and reduced intraarticular bone fragmentation of tunnel rims. The retrograde cutter is provided with a cutting blade that is configured to engage the shaft of the instrument and to lock onto the shaft.

8 Claims, 5 Drawing Sheets

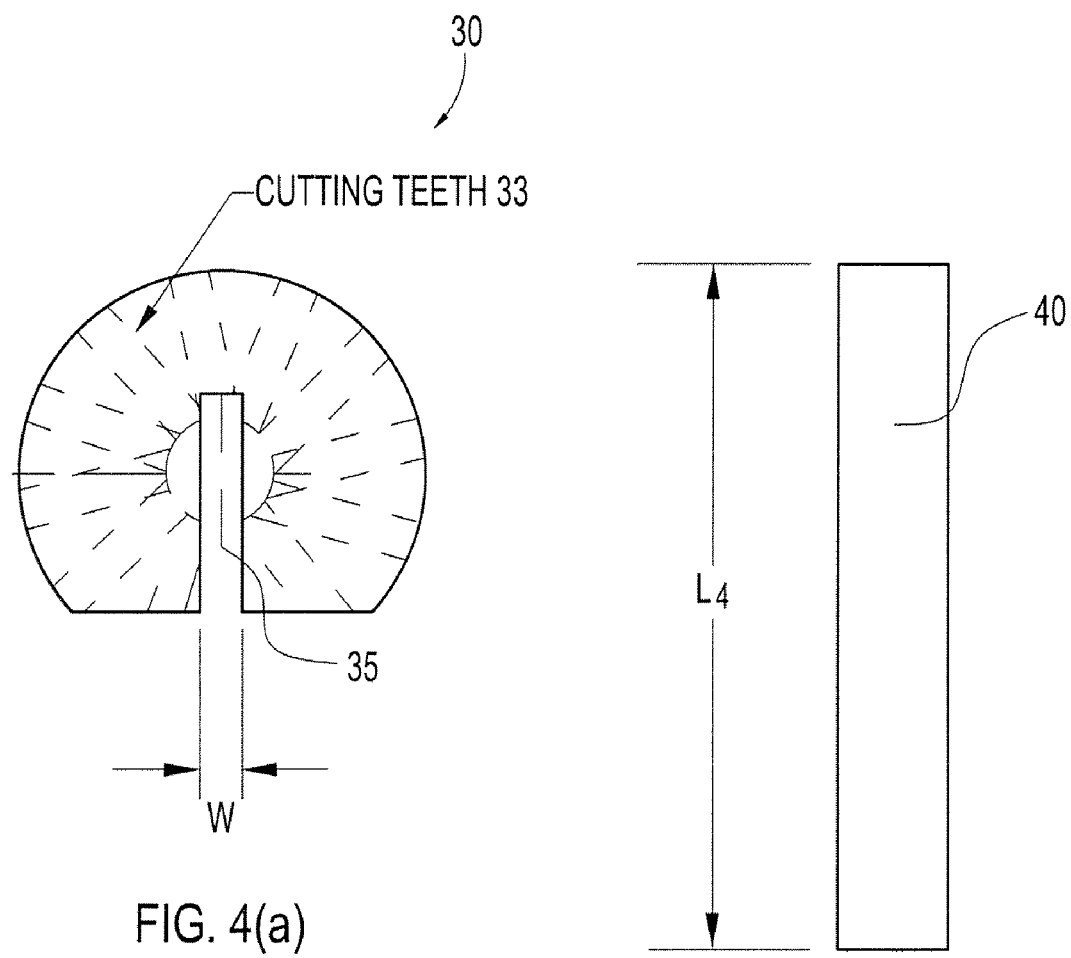
FIG. 4(a)
FIG. 5
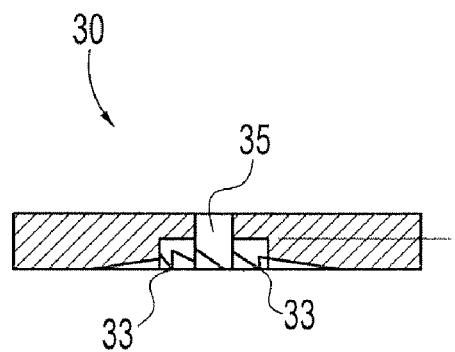
FIG. 4(b)

RETROGRADE CUTTING INSTRUMENT

CROSS REFERENCE TO RELATED APPLICATIONS

This application claims the benefit of U.S. Provisional Application Ser. No. 60/942,614 filed on Jun. 7, 2007, the entire disclosure of which is incorporated by reference in its entirety herein.

FIELD OF THE INVENTION

The present invention relates to arthroscopic surgical methods and instruments and, more specifically, to a retrograde cutting instrument and methods of retrograde repairs and reconstructions.

BACKGROUND OF THE INVENTION

During arthroscopic surgery, a small incision is made in the skin covering the arthroscopic site or joint so that surgical instruments may be placed in the joint and manipulated through arthroscopic visualization. As only a very small incision is made during arthroscopic surgery, it is often difficult to handle instruments within the joint capsule, where visibility and access to the structures of the joint capsule is minimal. It is also difficult to manipulate instruments during the formation of a recipient site socket (for example, a femoral or tibial tunnel) during reconstructive surgery, with minimal bone loss and reduced intraarticular bone fragmentation of tunnel rims.

Accordingly, a need exists for a surgical cutting instrument that is configured to allow improved handling of the instrument within a joint capsule, for example the knee capsule, during ACL reconstruction. A need also exists for a surgical cutter that is stable during knee arthroscopy and that provides drilling of femoral and tibial sockets or tunnels independently of one another and minimizes incisions of distal cortices and reduces intraarticular bone fragmentation of tunnel rims. Instruments and methods for creating a recipient site socket from the inside out, i.e., using a retrograde technique is also needed, as well as a technique for inserting a replacement osteochondral core or implant in recipient sockets formed in a retrograde manner.

SUMMARY OF THE INVENTION

The present invention provides a retrograde cutter that creates a recipient site socket from the inside out, i.e., using a retrograde technique, with minimal incisions of distal cortices and reduced intraarticular bone fragmentation of tunnel rims.

The retrograde cutter of the present invention is provided with a cutting blade that is configured to engage the shaft of the instrument and to lock into the shaft. The retrograde cutter of the present invention may be employed in a retrograde manner to form a recipient socket (to accommodate an osteochondral transplant, or to allow retrograde fixation of a graft within two sockets, for example).

Other features and advantages of the invention will become apparent from the following description of the invention, which refers to the accompanying drawings.

BRIEF DESCRIPTION OF THE DRAWINGS

FIG. 4(a) illustrates a top view of a blade of a cutter of the present invention.

FIG. 4(b) illustrates a cross-sectional view of the blade of FIG. 4.

FIG. 5 illustrates a cross-sectional view of a knurled nut of the cutter of the present invention.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a retrograde cutter that creates a recipient site socket from the inside out, i.e., using a retrograde technique, with minimal incisions of distal cortices and reduced intraarticular bone fragmentation of tunnel rims.

The retrograde cutter of the present invention is provided with a cutting blade that is configured to engage the shaft of the instrument and to lock into the shaft.

The retrograde cutter of the present invention may be employed in a retrograde manner to form a recipient socket (to accommodate an osteochondral transplant, or to allow retrograde fixation of a graft within two sockets, for example). As described in more detail below, formation of the recipient socket begins by inserting an outer tube and an inner tube of the instrument (together with a knurled nut) into the joint space, preferably from the outside in, through a small diameter tunnel. A cutting blade is then attached to the outer tube of the instrument by engaging the outer diameter of the instrument. The blade is locked into the instrument by engaging a locking mechanism (for example, a tongue) of the outer tube. A socket is created by conducting a drilling operation while the device is pulled in a retrograde manner.

Figure 8:
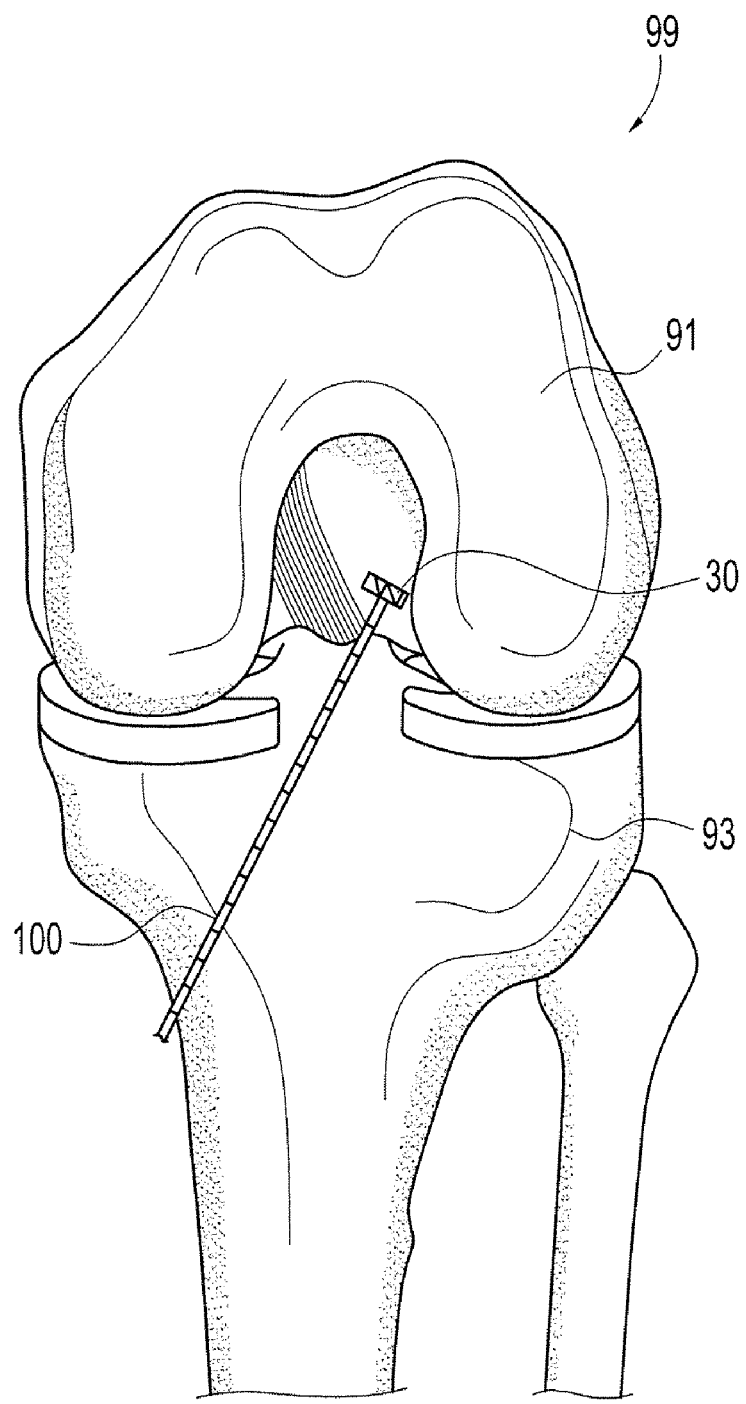
FIG. 8 schematically illustrates the formation of a socket with the cutter of the present invention.

Referring now to the drawings, where like elements are designated by like reference numerals, FIGS. 1-7 illustrate various views and various components of a retrograde cutter 100 of the present invention. FIG. 8 illustrates a schematic view of the retrograde cutter 100 of FIGS. 1-7 provided in the vicinity of a knee in which ACL reconstruction is conducted according to the present invention. The retrograde cutter 100 creates a recipient site socket from the inside out, i.e., using a retrograde technique, with minimal incisions of distal cortices and reduced intraarticular bone fragmentation of tunnel rims.

Figure 1:
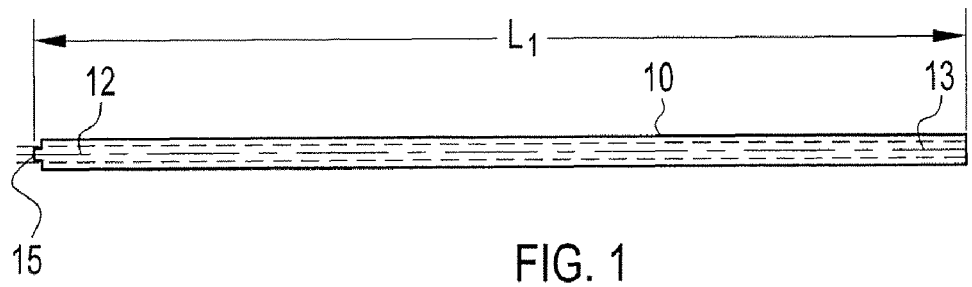
FIG. 1 illustrates a cross-sectional view of an outer tube of a cutter of the present invention.

As illustrated in FIGS. 1-7, retrograde cutter 100 (FIGS. 3, 6 and 7) includes a cannulated elongated outer tube 10 having a distal end 12 and a proximal end 13 (FIG. 1). Distal end 12 is provided (at its most distal part) with a locking mechanism 15 (for example, a protuberance or tongue 15) that is configured to engage a corresponding structure of blade 30 to be attached and securely engaged to the outer tube 10.

Figure 2:
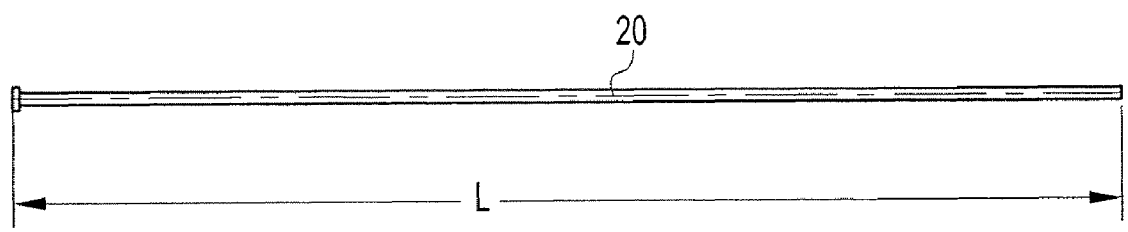
FIG. 2 illustrates a cross-sectional view of an inner tube of a cutter of the present invention.

The outer tube 10 of the retrograde cutter 100 houses an inner tube 20 (FIG. 2) with a diameter smaller than that of the outer tube 10. As shown in FIGS. 1 and 2, the outer tube 10 has a length $L_1$ which is smaller than length L of the inner tube 20 (length L also represents the total length of the instrument). The difference in lengths $L_1$ and L is represented by length $L_4$, which is the length of a knurled nut 40. Knurled nut 40 (FIG. 5) is configured to be removably attached to tubes 10 and 20, and to be actuated to allow engagement of cutting blade 30.

Figure 3:
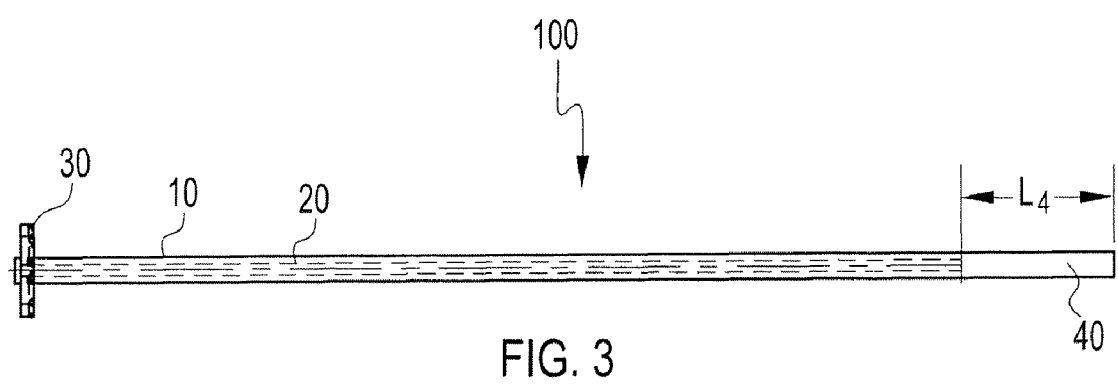
FIG. 3 illustrates a cross-sectional view of a cutter of the present invention, with the blade attached to the outer tube.
Figure 6:
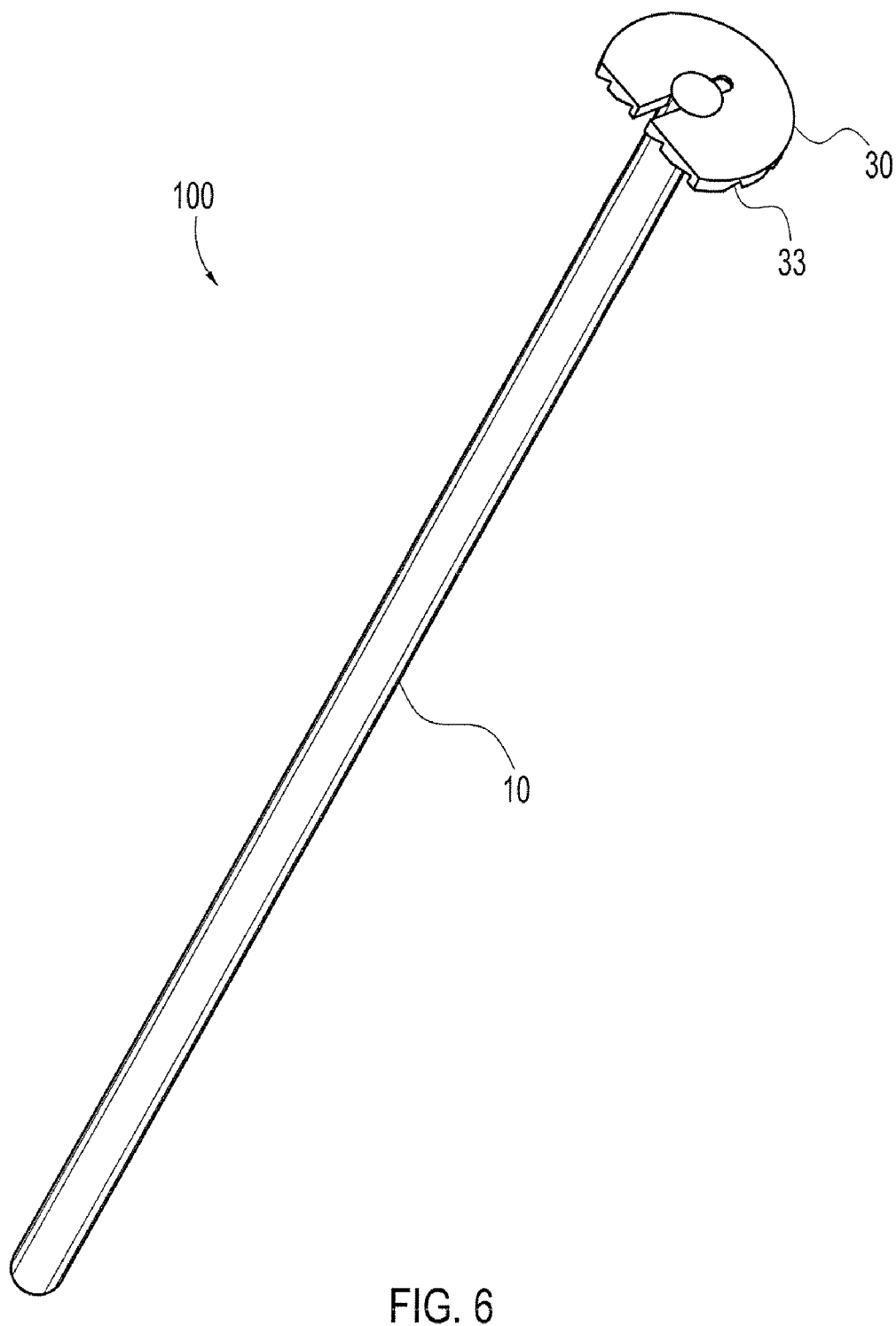
FIG. 6 illustrates a perspective view of the cutter of FIG. 3.
Figure 7:
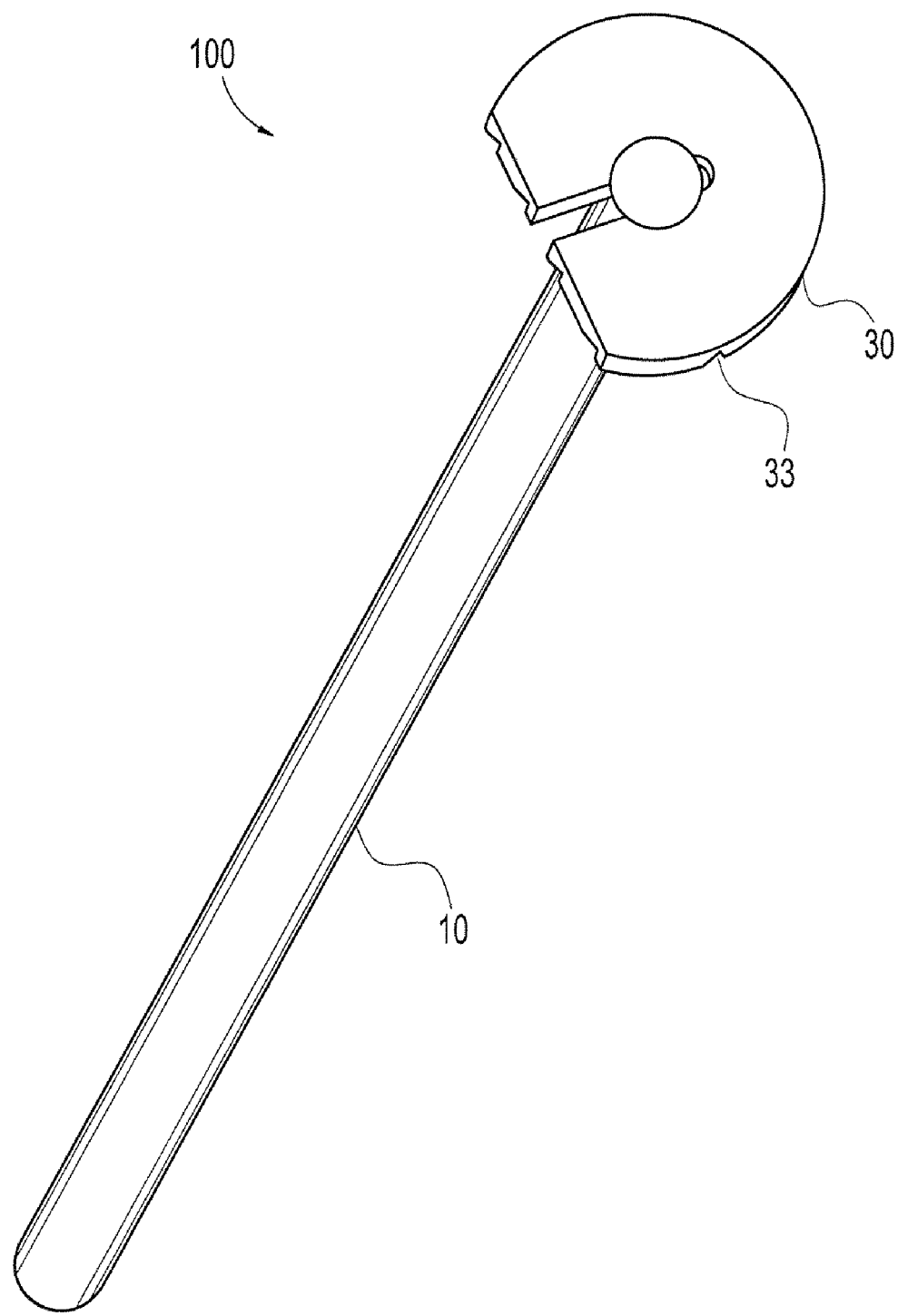
FIG. 7 illustrates another perspective view of the cutter of FIG. 3.

FIG. 3 illustrates cutter 100 with blade 30 provided at distal end 12 of the outer tube 10. Details of a specific exemplary embodiment of the blade 30 of the retrograde cutter 100 are illustrated in FIGS. 4(a)-(b); however, the invention contemplates other shapes and geometries for the blade 30.

Blade 30 illustrated in detail in FIGS. 4(a)-(b) has an overall circular or disk-like configuration. Blade 30 is configured to engage the shaft or outer tube 10 of the instrument 100 and to lock onto it. In an exemplary embodiment, blade 30 engages locking mechanism 15 (for example, tongue 15 as shown in FIG. 1) of shaft 10. A longitudinal slot 35 is provided through the blade 30 (fully extending from upper surface 32a to lower surface 32b) and for less than the diameter of the blade, as shown in FIGS. 4(a)-(b). The width W of the slot 35 is about equal to the width of tongue 15 of the outer tube 10, to allow secure engagement of the blade to the tube.

As also shown in FIGS. 4(ia)-(b), blade 30 is provided with a plurality of teeth 33 on a surface facing the proximal end of the outer tube 10 in the assembled state (i.e., on lower surface 32b of the blade 30).

In use, the outer tube 10, the inner tube 20 and the knurled nut 40 (FIG. 5) are inserted into a joint, from the distal side, until they are visible in the joint. The knurled nut 40 is unscrewed several turns and pushed proximally, until sufficient space is made available between outer tube 10 and inner tube 20 (to allow engagement of cutting blade 30).

Blade 30 is subsequently pushed into place (with cutting teeth 33 facing distally) to engage locking mechanism (tongue) 15 of the outer tube 10. The counter bore also engages the outside diameter of tube 10. The knurled nut 40 is then turned to draw inner tube 20 distally, therefore locking all parts of the retrograde cutting instrument 100 together.

Once the blade is locked onto cutting instrument 100, a drilling operation, for example, a retrograde drilling step, may be subsequently carried, as known in the art. According to an exemplary embodiment only, the retrograde cutter of the present invention may be employed in a retrograde manner to form a recipient socket (at the location of an osteochondral lesion developed on the head of the tibia, for example, or to accommodate retrograde fixation of a graft within two sockets). For example, FIG. 8 illustrates a schematic anterior view of a knee 99 with cutter 100 of FIGS. 1-7 in the vicinity of femur 91 and tibia 93. An exemplary method of ACL reconstruction may be performed according to an embodiment of the present invention by employing cutter 100 of FIGS. 1-7 to form at least one of a femoral and tibial socket. For example, with the instrument 100 oriented as shown in FIG. 8, a tibial socket or tunnel is formed within tibia 93 in a retrograde manner.

The present invention may be used to form various sockets or tunnels to allow fixation of a graft (for example, a semitendonosus allograft) or to allow replacement of osteochondral cores or implants in a retrograde manner, to obviate inserting harvesters into the joint. For example, cutting instrument 100 of the present invention may be employed for the formation of sockets during an "All-Inside ACL RetroConstruction" for ligament repair, developed by Arthrex, Inc. of Naples, Fla. (and disclosed in U.S. application Ser. No. 60/947,290, the disclosure of which is herein incorporated by reference), which comprises, for example, the steps of: (i) drilling at least one of a femoral and tibial tunnel or socket using a retrodrill technique employing the cutting instrument 100 of FIGS. 1-7; (ii) providing a graft (soft tissue graft or BTB graft) in the vicinity of the sockets; and (iii) securing the graft within the femoral and tibial tunnels (sockets).

According to yet another embodiment, an exemplary method of ACL retrograde reconstruction of the present invention comprises, for example, the steps of: (i) drilling a femoral socket; (ii) drilling a tibial tunnel or socket using a retrodrill technique employing the cutting instrument 100 of FIGS. 1-7; (iii) providing a graft (soft tissue graft or BTB graft) in the vicinity of the sockets; (iv) securing the graft (soft tissue graft or BTB graft) to a continuous loop/button construct comprising a button with an oblong configuration and provided with an inside eyelet that allows the passage of the continuous loop, preferably a suture loop; (v) passing the graft with the button through the femoral tunnel; (vi) securing the button to the femoral cortex once the button exits the femoral socket; and (vii) securing the graft in the tibial tunnel or socket.

Although the above-detailed methods of socket formation using the cutter 100 of the present invention have been described with reference to a specific ACL reconstruction (i.e., a specific "All-Inside ACL RetroConstruction" for ligament repair), the invention is not limited to this exemplary embodiment, and contemplates any repairs and reconstructions that employ a cutting instrument such as cutter 100 of the present invention.

Although the present invention has been described in relation to particular embodiments, many other variations and modifications and other uses will become apparent to those skilled in the art. It is preferred, therefore, that the present invention be limited not by the specific disclosure herein, but only by the appended claims.

What is claimed as new and desired to be protected by Letters Patent of the United States is:

1. A method of conducting arthroscopic surgery comprising:
    inserting a retrograde cutting instrument into a joint cavity in the vicinity of at least a bone, the cutting instrument having a proximal end and a distal end, the cutting instrument comprising an outer tube having a distal end, and an inner tube located within the outer tube;
    attaching a blade to the cutting instrument within the joint cavity so that the blade releasably engages a locking mechanism of the distal end of the outer tube and is releasably secured between the inner tube and the distal end of the outer tube, the blade having a circular, disk-shaped configuration and comprising two opposed sides with two opposed surfaces, only one of the two opposed surfaces being a cutting surface provided with a plurality of teeth and facing the proximal end of the cutting instrument; and
    forming a socket into the bone in a retrograde manner, using the cutting instrument.

2. The method of claim 1, wherein the bone is tibia.

3. The method of claim 1, further comprising the steps of:
    forming a socket in an adjacent bone in an antegrade manner; and
    securing the ends of a graft respectively in the sockets of the bone and of the adjacent bone.

4. The method of claim 1, further comprising inserting the retrograde cutting instrument into the joint cavity so that the cutting surface of the blade faces the bone.

5. The method of claim 1, wherein the two opposed surfaces are an upper surface and a lower surface of the blade.

6. A method of knee reconstruction comprising:

providing a retrograde cutter having an outer elongated tube with a distal end, an inner tube located within the outer elongated tube, the inner tube being provided with a radially projecting flange at its most distal end, and a blade with a substantially disk-shape configuration, the blade comprising two opposed sides with two opposed surfaces, only one of the two opposed surfaces being a cutting surface provided with a plurality of teeth;

inserting the outer elongated tube and inner tube of the retrograde cutter into a knee joint cavity;

attaching the blade to the retrograde cutter within the joint cavity so that the blade releasably engages a locking mechanism of the distal end of the outer elongated tube and is releasably secured between the flange of the inner tube and the distal end of the outer tube, the blade being oriented so that the cutting surface of the blade faces a proximal end of the cutter and is configured to cut in a retrograde manner; and retrograde cutting into a tibia to form a socket in the tibia in a retrograde manner, using the retrograde cutter.

7. The method of claim 6, further comprising the steps of forming a socket in a femur in an antegrade manner; and securing the ends of a graft respectively in the sockets of the tibia and femur.

8. The method of claim 6, wherein the socket is formed to a depth of about 30 mm to about 40 mm.

* * * * *